April 26, 1966 M. L. MEILLAND Plant Pat. 2,625
ROSE PLANT
Filed Feb. 3, 1965
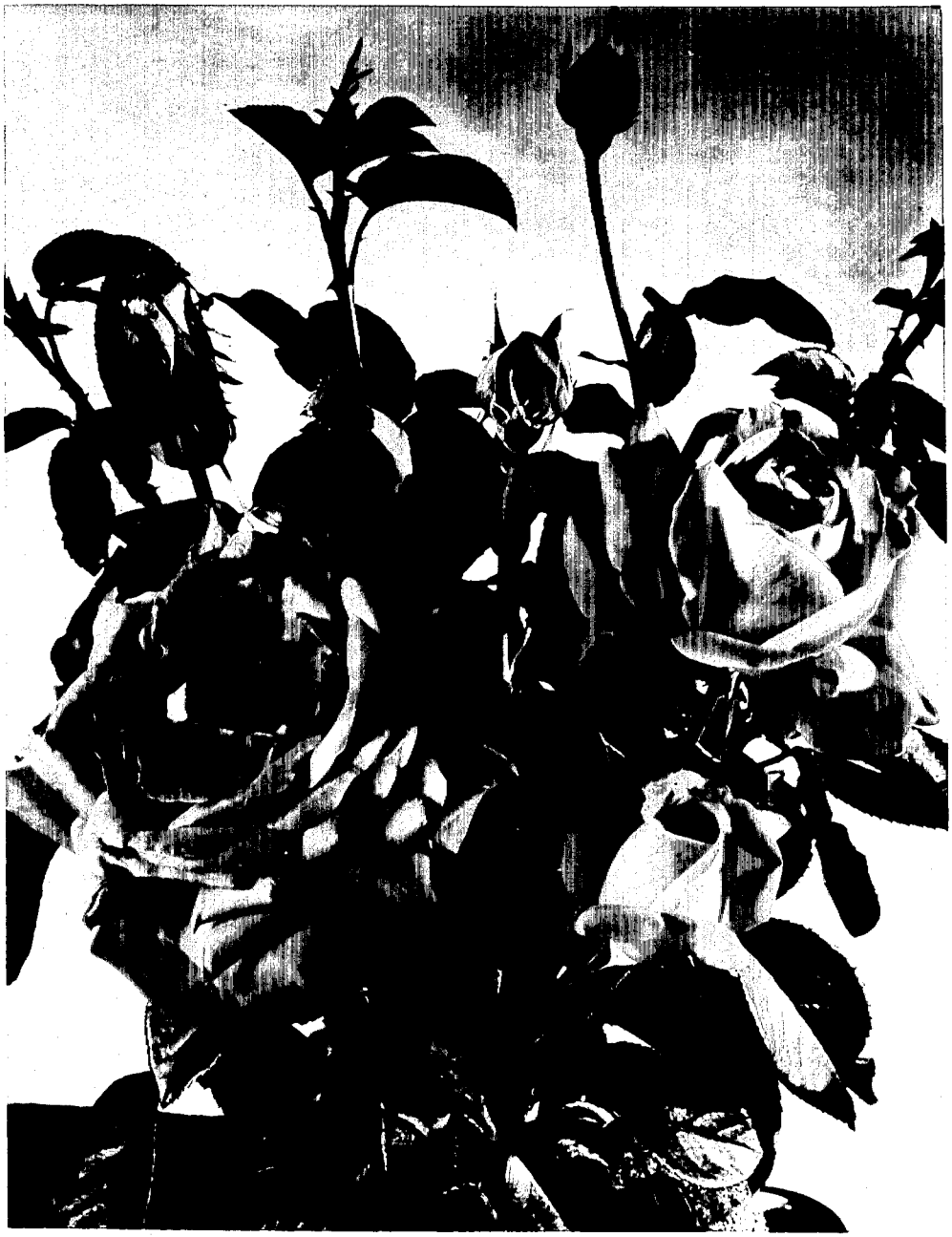
Inventor.
Marie Louise Meilland
By: Robb & Robb
Attorneys.

United States Patent Office

Plant Pat. 2,625
Patented Apr. 26, 1966

2,625
ROSE PLANT

Marie Louise Meilland, Cap d'Antibes, Alpes-Maritimes, France, assignor to The Conard-Pyle Company, West Grove, Pa., a corporation of Pennsylvania Filed Feb. 3, 1965, Ser. No. 430,230
Claims priority, application France, July 30, 1964, 45,027
1 Claim. (Cl. Plt.—20)

The present invention relates to a new and distinct variety of rose plant of the hybrid tea class, which was originated by me by crossing the variety "Chrysler Imperial" (U.S. Plant Patent No. 1,167) with the variety "Karl Herbst" (unpatented).

The primary objectives of this breeding were to produce a new rose variety of the hybrid tea class which has a more uniform habit of growth, with vigorous and well balanced branches bearing foliage having good resistance to the usual rose diseases, particularly to blackspot, and which bears large flowers of a general Crimson Red color different from other hybrid tea varieties previously known, combined with the ability to rebloom quickly. These objectives were fully achieved along with other desirable improvements, as evidenced by the following unique combination of characteristics which are outstanding in the new variety and which distinguish it from its parents, as well as from all other varieties of which I am aware:

(1) Vigorous, uniform and bushy habits of growth;
(2) A continuous blooming habit;
(3) Double, strongly fragment flowers having firm petals and being of good form;
(4) A distinctive and attractive Tyrian Purple flower color which shades to Solferino Purple as the flower ages;
(5) Long-lasting flower qualities;
(6) A clean dropping habit of the flower petals; and
(7) Good resistance to the usual rose diseases, particularly to blackspot.

Asexual reproduction of the new variety by budding, as performed in France and also at West Grove, Pennsylvania, U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; outdoor; seedling; for garden decoration.
Class: Hybrid tea.
Breeding: Seedling.
*Seed parent.*—"Chrysler Imperial."
*Pollen parent.*—"Karl Herbst."
Propagation: Holds its distinguishing characteristics through succeeding propagations by budding.

*Flower*

Locality where grown and observed: West Grove, Pennsylvania, U.S.A.
Flowers borne: Usually singly, but occasionally two or more to stem; on strong stems of medium length.
Quantity of bloom: Free, outdoors.
Continuity: Continuous.

Fragrance: Strong. Nature—tea.
Bud:
*Peduncle.*—Medium length; medium caliper; stiff; rough with numerous glandular red hairs. Color.—Reddish.
*Before calyx breaks.*—Size—large. Form—pointed ovoid; with a conspicuous neck; with foliaceous appendages on the surface of the bud; with bristle-like foliaceous parts extending beyond the tip of the bud equal to ¼ or more of its length.
*As calyx breaks.*—Color—Beetroot Purple, Plate 830.
*As first petal opens.*—Size—large. Form—medium length; urn-shaped. Color—outside — Solferino Purple, Plate 26 where exposed to light, with protected areas shaded with Dianthus Purple, Plate 730, and with point of attachment Barium Yellow, Plate 503; inside—Rose Bengal, Plate 25, with point of attachment Aureolin, Plate 3.
*Opening.*—Opens up well.
Bloom:
*Size (when fully open).*—Large; from 4½ inches to 5 inches.
*Petalage.*—Very double; from 50 to 60 petals; arranged regularly.
*Form.*—Cupped at first and remaining cupped; petals being at first loosely rolled outward and remaining loosely rolled outward at maturity.
Petals:
*Texture.*—Medium thickness; leathery.
*Appearance.*—Inside—satiny. Outside—shiny.
*Shape.*—Outer—obovate. Intermediate — obovate. Inner—obovate.

This description of a newly opened flower was made from a rose grown outdoors during the month of September at West Grove, Pennsylvania, U.S.A.:

*Color.*—Outer petal—outside surface—Tyrian Purple, Plate 727/3, with point of attachment Barium Yellow, Plate 503; inside surface—Solferino Purple, Plate 26 over upper ¾ of petal, then becoming progressively tinted with Tyrian Purple, Plate 727/3 toward the base of the petal, with point of attachment Aureolin, Plate 3. Intermediate petal—outside surface—Spinel Pink, Plate 0625, with point of attachment Barium Yellow, Plate 503; inside surface—Tyrian Purple, Plate 727/3, with point of attachment Aureolin, Plate 3, becoming blended into the dominant petal color. Inner petal—outside surface—Spinel Pink, Plate 0625, with point of attachment Barium Yellow, Plate 503; inside surface—Tyrian Purple, Plate 727/2, with point of attachment Aureolin, Plate 3, becoming blended into the dominant petal color.

This description was made of a rose that was open for three days outdoors during the month of September at West Grove, Pennsylvania, U.S.A.:

*Color.*—Outer petal—outside surface—Solferino Purple, Plate 26/1, with point of attachment Barium Yellow, Plate 503; inside surface—Solferino Purple, Plate 26, with point of attachment Aureolin, Plate 3, blending into the dominant petal color. Inner petal—outside surface—Solferino Purple, Plate 26/2, with point of attachment Barium Yellow, Plate 503; inside surface—Solferino Purple, Plate 26/1, with point of attachment Aureolin, Plate 3, blending into the dominant petal color.
*General color effect.*—Newly opened flower—Tyrian Purple, Plate 727/2. 3-days open—Solferino Purple, Plate 26/1.

*Behavior.*—Drop off cleanly.

*Flower longevity.*—On bush in garden—4 days in September. Cut roses grown outdoors and kept at living room temperatures—4 days in September.

*Reproductive organs*

Stamens: Many; arranged regularly about pistils; mixed with petaloids.

Filaments: Many; medium length; most with anthers. Color—Yellow at base, becoming suffused with pink toward anthers.

Anthers: Open at various times; medium size; occasionally an anther fused with a petaloid. Color—yellow.

Pollen: Moderate abundance. Color—yellow.

Pistils: Many.

Styles: Uneven; medium length; medium caliper; bunched.

Stigma: Color—White Yellow.

Ovaries: Some protruding from receptacle.

Hips: None observed.

Sepals: Permanent; moderately long; spear-shaped.

Seeds: None observed.

*Plant*

Foliage:

*Leaves.*—Compound of usually 5 but sometimes 7 leaflets; abundant; moderately large; leathery.

*Leaflets.*—Shape—from round to oval. Apex—obtuse, but usually acute. Base—round. Margin—simply serrate.

*Color.*—Mature—upper surface—Ivy Green, Plate 0001060/1; under surface—Sage Green, Plate 000861. Young—upper surface—Parsley Green, Plate 00962, overlaid with Maroon, Plate 1030; under surface—Maroon, Plate 1030/2.

*Rachis (the supporting stem of the compound leaf).*—Medium caliper. Upper side—grooves; hairy; prickly. Under side—moderately prickly.

*Stipules.*—Moderately long; medium width; with points of medium length, turning out at an angle of 45°.

*Disease resistance.*—Comparable to that of the average rose variety grown under the same cultural conditions at West Groove, Pennsylvania, U.S.A., but especially good resistance to Blackspot.

Growth:

*Habit.*—Bushy; much-branched.

*Growth.*—Free.

*Canes.*—Moderately heavy.

*Main stems.*—Dull. Color—Spinach Green, Plate 0960/1. Prickles — several; color — Brown. Hairs—none.

*Branches.*—Dull. Color—Spinach Green, Plate 0960/1. Prickles — several; color — Greenish Brown. Hairs—none.

*New shoots.*—Dull. Color—Fern Green, Plate 0826, overlaid with Maroon, Plate 1030. Prickles—several; Color—Maroon. Hairs—none.

I claim:

A new and distinct variety of rose plant of the hybrid tea class, substantially as herein shown and described, characterized particularly as to novelty by the unique combination of a vigorous, uniform and bushy habit of growth, a continuous blooming habit, double, strongly fragrant flowers having firm petals and being of good form, a distinctive and attractive Tyrian Purple flower color which shades to Solferino Purple as the flower ages, long-lasting flower qualities, a clean dropping habit of the flower petals, and good resistance to the usual rose diseases, particularly to blackspot.

No references cited.

ANTONIO F. GUIDA, *Acting Primary Examiner.*

ROBERT E. BAGWILL, *Assistant Examiner.*